US007705184B2

(12) United States Patent
Buenger et al.

(10) Patent No.: US 7,705,184 B2
(45) Date of Patent: Apr. 27, 2010

(54) METHOD OF MAKING AMPHETAMINE

(75) Inventors: Greg Buenger, Charles City, IA (US); Jason Douglas, Charles City, IA (US); Paul Jass, Charles City, IA (US); Erik Michalson, Charles City, IA (US); Matthew Schiesher, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 0 days.

(21) Appl. No.: 12/466,457

(22) Filed: May 15, 2009

(65) Prior Publication Data

US 2009/0292143 A1 Nov. 26, 2009

Related U.S. Application Data

(60) Provisional application No. 61/054,641, filed on May 20, 2008.

(51) Int. Cl.
*C07C 209/74* (2006.01)
(52) U.S. Cl. ...................................... 564/381
(58) Field of Classification Search ........................ None
See application file for complete search history.

(56) References Cited

U.S. PATENT DOCUMENTS

| 4,967,031 A | 10/1990 | Bullock |
| 5,962,737 A | 10/1999 | West |
| 6,399,828 B1 | 6/2002 | Boswell et al. |

OTHER PUBLICATIONS

Masayasu Tomie et al., Synthesis of Optically Active Prenylamine from (−)-Norephedrine. Chem. Pharm. Bull., 24(5), pp. 1033-1039, 1976.
Ladislav Kniezo et al., Stereochemical Course of the Reaction of 2-Haloethyl Isothiocyanates with Nucleophiles, Stereospecific Route to 4,5-DisubstitutedΔ2-Thiazolines and Thiazolidine-2-Thiones, Collection of Czechoslovak Chemical Communications, Czechoslovak Academy of Sciences, vol. 46, pp. 717-728, Mar. 1981.
Angelina Flores-Parra et al., Chlorination reactions of ephedrines revisited. Stereochemistry and functional groups effect on the reaction mechanisms, Tetrahedron: Asymmetry 9, pp. 1661-1671, 1998.

*Primary Examiner*—Brian J Davis
(74) *Attorney, Agent, or Firm*—Banner & Witcoff, Ltd.

(57) ABSTRACT

A method in which a crude chlorinated product of a phenylpropanolamine, preferably prepared by reacting thionyl chloride with the phenylpropanolamine, is purified by contacting an aqueous solution of the crude product with carbon. The carbon-treated solution of the crude chlorinated product of a phenylpropanolamine is catalytically hydrogenated to the corresponding amphetamine derivative.

15 Claims, No Drawings

METHOD OF MAKING AMPHETAMINE

CROSS REFERENCE TO RELATED APPLICATIONS

This is a U.S. Non-Provisional Patent Application which claims priority to U.S. Provisional Patent Application Ser. No. 61/054,641, filed May 20, 2008, the entire contents of which are incorporated herein by reference.

BACKGROUND OF THE INVENTION

1. Field of the Invention

The invention relates to the preparation of d- or d,l-amphetamines.

2. Description of Related Art

U.S. Pat. No. 6,399,828 identifies two prior art techniques for synthesizing amphetamine from norephedrine.

In one approach, norephedrine first is refluxed with hydrogen iodide and red phosphorus. In the other approach, norephedrine is chlorinated using thionyl chloride and then the chlorinated product, following recrystallization from a methanol-isopropyl ether solution, is subjected to hydrogenolysis (catalytic hydrogenation) over a palladium-on-carbon catalyst.

Tomie et al., Chem. Pharm. Bull., Vol. 24, No. 5, pp. 1033-1039 (1976) describes a synthesis of threo-2-amino-1-chloro-1-phenylpropane from norephedrine by reaction with thionyl chloride in chloroform (trichloromethane—$CHCl_3$). Following in vacuo concentration and an ether wash, the product was recrystallized from an ethanol solution.

Kniežo et al., Collection Czechoslovak Chem. Commun., Vol. 46, No. 3, pp. 717-724 (1981) describes a synthesis of threo-1-chloro-1-phenyl-2-propylammonium chloride from norephedrine by reaction with thionyl chloride in benzene ($C_6H_6$). Following vacuum concentration ("the mixture was taken down"), the product was recrystallized from an ethanol solution.

Workers continue to look for improved ways of making amphetamines, such as from phenylpropanolamines, such as norephedrine.

DESCRIPTION OF THE INVENTION

The present invention provides a cost-effective method of preparing d- or d,l-amphetamine free bases, or salts thereof of high purity. Amphetamine is a well-known stimulant. A d- or d,l-amphetamine free base prepared according to the invention also is useful in animal models. For example, the d- or d,l-amphetamine free base can be dissolved in a physiologically acceptable solvent, such as saline, and used to challenge experimental animals in in vivo models of motor coordination and agility. Such materials also provide useful starting materials for the synthesis of other valuable chemicals, including pharmaceuticals This invention provides an improved method of making d- or d,l-amphetamine (1-methyl, 2-phenyl ethylamine; 2-amino-propylbenzene), methamphetamine and related amphetamine compounds from phenylpropanolamines.

The invention specifically relates to an improved method for making amphetamine-related products of formula (I):

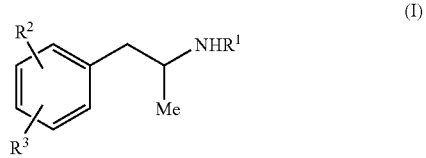

(I)

where $R^1$ is hydrogen or a lower alkyl group, and $R^2$ and $R^3$ are independently selected from hydrogen, halogen, lower alkyl groups, lower alkoxy groups, lower alkyl groups substituted with 1 to 5 halogens, lower alkoxy groups substituted with 1 to 5 halogens, or both $R^2$ and $R^3$, when on adjacent carbons, together constitute —$O(CH_2)_xO$— where x is an integer of 1 to 4, thereby forming a ring structure fused with the phenyl group, the method comprising:

dissolving a crude chlorinated phenylpropanolamine hydrochloride product of formula (II):

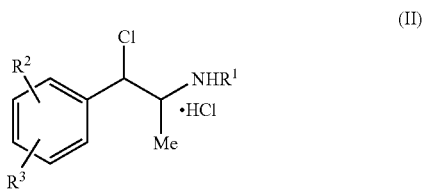

(II)

where $R^1$, $R^2$ and $R^3$ have the same meanings as identified above in connection with formula (I), in water to form an aqueous solution, contacting the aqueous solution with carbon and hydrogenating the carbon-treated aqueous solution.

The invention particularly relates to a method in which a crude chlorinated product of a phenylpropanolamine, prepared by reacting thionyl chloride with a phenylpropanolamine, is purified and then catalytically hydrogenated to the corresponding amphetamine derivative.

A crude chlorinated product of a phenylpropanolamine can be prepared by slowly charging thionyl chloride to a solution of the phenylpropanolamine. Toluene, a more pharmaceutically acceptable material, is preferably used as the solvent for the phenylpropanolamine, rather than either benzene or chloroform (trichloromethane), as reported in the aforementioned chemical literature. Toluene also is advantageous in that the chlorinated phenylpropanolamine hydrochloride product tends to be less soluble (i.e., more insoluble) in toluene, particularly at below ambient temperatures. Thus the chlorinated phenylpropanolamine precipitates readily from the reaction mixture making it convenient to isolate the chlorinated product.

In any event, a chlorinated phenylpropanolamine hydrochloride product is isolated from the chlorination reaction mixture by causing it to precipitate, filtering the precipitated solids and washing the solids with additional solvent, preferably toluene, to remove residual impurities.

In accordance with the present invention, the so-isolated, crude chlorinated phenylpropanolamine hydrochloride then is dissolved in purified water and contacted with carbon (e.g., active carbon). Contacting can easily be accomplished by filtering the aqueous solution of the crude chlorinated phenylpropanolamine hydrochloride through a bed of carbon. In this approach, the carbon, in a particulate form, is usually retained on a filter. Preferably, the filter bed also includes some diatomaceous earth (e.g., Celatom). The bed of solids (including the carbon and the diatomaceous earth) retained on the filter is washed with additional water, and the recovered filtrates are transferred directly to a hydrogenation reactor.

The hydrogenation reaction is conducted with the aqueous solution of the chlorinated phenylpropanolamine hydrochloride product recovered from the carbon (e.g., carbon filtration) treatment. A palladium-on-carbon catalyst is added to the hydrogenation reactor. The solution in the reactor is stirred and the hydrogenation reaction proceeds at a temperature of 20 to 55° C. under a hydrogen atmosphere. An atmosphere of hydrogen at a pressure of 15 to 50 psi, e.g., about 40 psi, should be suitable. Establishing a suitable condition of temperature and pressure is within the skill of the art and the particular conditions are not narrowly critical. The progression of the reaction can be monitored using HPLC. As shown in Examples 3 and 4, the hydrogenation also can be conducted under conditions that minimize the risk of corrosion in 316 stainless steel reactors. Once the hydrogenation is completed, the catalyst can be filtered from the reaction solution. The recovered solids, mostly catalyst, are then washed with additional water, and the wash is combined with the aqueous hydrogenated product.

A crude amphetamine product then is isolated and recovered from the resulting aqueous hydrogenated product simply by adjusting the pH of the aqueous solution to greater than about 12 with an inorganic base, preferably sodium hydroxide. This generates the free amphetamine base which is immiscible with the aqueous phase. The separately formed organic phase is then separated from the aqueous phase. The organic phase can be purified by a simple vacuum distillation.

Thus, the present invention comprises a method for making amphetamine-related products of formula (I):

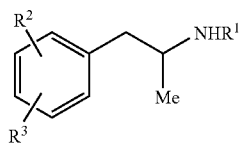

(I)

where $R^1$ is hydrogen or a lower alkyl group, and $R^2$ and $R^3$ are independently selected from hydrogen, halogen, lower alkyl groups, lower alkoxy groups, lower alkyl groups substituted with 1 to 5 halogens, lower alkoxy groups substituted with 1 to 5 halogens, or both $R^2$ and $R^3$, when on adjacent carbons, together constitute —O(CH$_2$)$_x$O— where x is an integer of 1 to 4, thereby forming a ring structure fused with the phenyl group; in which a crude chlorinated phenylpropanolamine hydrochloride product of formula (II):

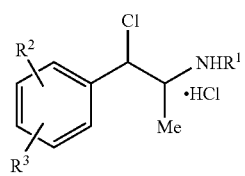

(II)

where $R^1$, $R^2$ and $R^3$ have the same meanings as identified above in connection with formula (I), is dissolved in water, the aqueous solution is contacted with carbon, such as by filtering the aqueous solution through a bed of carbon, preferably also containing diatomaceous earth, the so-filtered aqueous solution is then hydrogenated, the resulting free base of the hydrogenated product then is isolated by a phase separation, following a pH adjustment of the aqueous hydrogenated product and the so-isolated free base can be purified by vacuum distillation.

As used herein, the term "lower alkyl groups" means a branched or straight-chain saturated aliphatic hydrocarbon monovalent radical having 1-8 carbon atoms. This term is exemplified by groups such as methyl, ethyl, n-propyl, 1-methylethyl (isopropyl), n-butyl, n-pentyl, 1,1-dimethylethyl (tert-butyl), and the like.

The term "lower alkoxy groups" means a monovalent radical of the formula AlkO— where Alk is a lower alkyl group. This term is exemplified by groups such as methoxy, ethoxy, propoxy, isopropoxy, butoxy, sec-butoxy, tert-butoxy, pentoxy, and the like.

Halogen means one or more of fluorine (F); chlorine (Cl); bromine (Br) and iodine (I), preferably fluorine or chlorine.

In preferred practice, the chlorinated phenylpropanolamine hydrochloride product of formula (II) is prepared by reacting a solution of a phenylpropanolamine of formula (III) (preferably in toluene) with thionyl chloride:

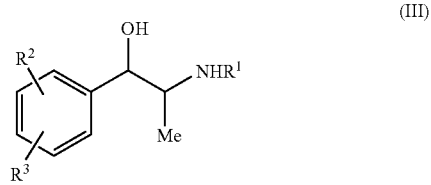

(III)

The reaction is preferably conducted by slowing charging the thionyl chloride into a stirred solution of the phenylpropanolamine in toluene. The reaction is stirred at a temperature of 55 to 60° C. for 3-6 hours. The reaction conversion can be determined by HPLC.

By using toluene as a solvent, the chlorinated salt product produced by the reaction between the dissolved phenylpropanolamine and the thionyl chloride is insoluble. Thus, the chlorinated phenylpropanolamine hydrochloride product, especially on cooling of the toluene solvent to about 10° C., readily precipitates from the solution. The chlorinated product solids can then be easily recovered by filtration and then washed with additional toluene to remove soluble impurities. Drying the recovered solids in a vacuum oven yields a crude chlorinated phenylpropanolamine hydrochloride product. Following treatment in accordance with the present invention, the so-treated crude chlorinated phenylpropanolamine hydrochloride product serves as the starting material for the catalytic hydrogenation of the present invention.

In accordance with the present invention, the crude chlorinated phenylpropanolamine hydrochloride product is dissolved in water and is treated to remove contaminants that interfere with the subsequent catalytic hydrogenation. Applicants discovered that if the crude chlorinated product recovered after the toluene wash is used directly in the catalytic hydrogenation, then the conversion to the desired amphetamine derivative is very poor. In the case where a crude threo-2-amino-1-chloro-1-phenylpropane hydrochloride was catalytically hydrogenation, after six (6) hours, the reaction mixture contained the starting chloroamphetamine to the desired d-amphetamine in a ratio of only 6:93.

According to the present invention, the aqueous solution of the crude chlorinated phenylpropanolamine hydrochloride product is contacted with carbon. This contacting can be accomplished conveniently by passing the aqueous solution through a carbon bed (activated carbon), preferably containing a diatomaceous earth as well, such as Celatom®. Preferably, an amount of carbon constituting from about 2 to 25% by weight of the mass of the crude chlorinated product is used for contacting the aqueous solution. For example, if the crude chlorinated product weighs 10 grams, then the aqueous solution prepared using the crude chlorinated product should be filtered through a bed of about (or otherwise contacted with about) 0.2 to 2.5 grams of carbon.

The aqueous filtrate recovered from the carbon treatment then is subjected to catalytic hydrogenation. While a variety of precious metals can be used for catalyzing the hydrogenation reaction, including platinum, palladium, ruthenium, osmium, iridium, rhodium, and the like, or mixtures thereof. Palladium on a carbon support is a convenient choice. Broadly, the catalytic metal or alloy can be provided in the form of a finely divided powder or granules, or can be deposited on a support of high surface area such as carbon, activated carbon, silica, alumina, or another metal oxide. Usually, the supported precious metal is preferably present at 0.5 wt. % to 10 wt. % on the support.

The aqueous solution of the carbon-treated, chlorinated phenylpropanolamine hydrochloride product is charged to a suitable reactor with the catalyst and mixed under a hydrogen atmosphere. Hydrogen at a pressure of about 25-50 psi should be suitable. The reaction can be conducted at a temperature in the range of 45 to 55° C. The reaction is normally complete in about 4 to 24 hours. The reaction conversion can be determined by HPLC.

Following the completion of the reaction, the reaction mixture is filtered to remove the catalyst, e.g., the palladium on carbon catalyst, the filtrate is basified, for example using sodium hydroxide, though other inorganic bases could be used, and the resulting aqueous layer can be separated from the amphetamine layer. The amphetamine layer can then be vacuum distilled to remove residual impurities.

The above disclosure generally describes the present invention. A more complete understanding can be obtained by reference to the following specific embodiment, which is provided for purposes of illustration only and is not intended to limit the scope of the invention.

EXAMPLE 1

Chlorination 200 g of 1-norephedrine and 2075 g of toluene are charged to a reaction flask. The solution is stirred while slowly adding a charge of 197.4 g of thionyl chloride. The reaction mixture so-formed is stirred at 55-60° C. for 3-6 hours. The reaction conversion is determined by HPLC. The reaction mixture is cooled to less than 10° C. with stirring and chlorodextroamphetamine hydrochloride precipitates. The precipitated solids are isolated by filtration and washed twice with 865 g of toluene. The product wet cake is dried in a vacuum oven to yield 252 g (92%) of a crude chlorodextroamphetamine hydrochloride.

EXAMPLE 2

Hydrogenation 150 g of the crude chlorodextroamphetamine hydrochloride produced in Example 1 is dissolved in a flask using 325 g of water. The aqueous solution of chlorodextroamphetamine hydrochloride is filtered through a bed of carbon and Celatom retained on a filter. The carbon bed is washed with water, and all the filtrates are charged into a reaction vessel along with 10.5 g of 10% palladium on carbon (50% wet) catalyst. The reaction mixture is stirred at 45-55° C. under 40 psi of hydrogen. The reaction conversion is determined by HPLC. The catalyst is filtered from the recovered reaction mixture and the catalyst filter cake is washed with water. The pH of the filtrate is adjusted to greater than pH 12 with sodium hydroxide. Crude dextroamphetamine forms an organic phase which is isolated from the aqueous phase. The dextroamphetamine crude product is then purified by vacuum distillation.

EXAMPLE 3

Hydrogenation

In this example, previously purified chlorodextroamphetamine hydrochloride was hydrogenated under acidic conditions to demonstrate that the hydrogenation could safely be conducted in a 316 stainless steel hydrogenator.

Into a 50-mL reactor fitted with a 3-way valve for gas introduction and also equipped with magnetic stirrer and a gas reservoir at atmospheric pressure, was added (1) chlorinated intermediate (chloro-D-amphetamine hydrochloride; 2.06 parts by weight) such as produced in accordance with Example 1, (2) acetic acid (20.6 parts by weight), and (3) sodium acetate (2.06 parts by weight). A solution was established by adding 4 parts by weight water at about 20° C.

Then 0.2 parts by weight of 10% w/w Pd/C (50% water wet) was charged into the flask to give a black suspension. After evacuative purging of the gas space of the flask with hydrogen/vacuum (6 times), the reaction mixture was stirred at about 20° C. with a $H_2$ reservoir at about 15 psi (e.g., balloon pressurized hydrogen atmosphere). After about 3 hours, the reaction was about 25% complete. After about 33 hours, HPLC indicated complete conversion to D-amphetamine. The catalyst was easily removed via filtration to give a clear solution for further processing.

EXAMPLE 4

Hydrogenation

Into a glass vessel with magnetic stirring, 4.12 g of a crude D-chloroamphetamine hydrochloride was charged (prepared per Example 1), along with 10 g of water, and 0.42 g of carbon. The carbon slurry was filtered through Celatom to clarify. Then 0.25 g of a 10 wt % Pd/C catalyst (50 wt % water wet) was charged into the vessel along with 3.6 g sodium acetate, and 8.5 g acetic acid. The vessel was purged with hydrogen and stirred at ~20° C. under a hydrogen atmospheric at about 15 psi (e.g., balloon pressurized hydrogen atmosphere). The extent of the reaction was monitored by HPLC analysis. After ~3.5 hours, the reaction was ~20% complete. After ~26 hours, the reaction was >99% complete.

While the invention has been described with reference to certain preferred embodiments, and exemplified with respect thereto, those skilled in the art will appreciate that various changes, substitutions, modifications and omissions may be made without departing from the spirit of the invention. Accordingly, it is intended that the scope of the present invention be limited solely by that of the following claims. Unless otherwise specifically indicated, all percentages are by weight. Throughout the specification and in the claims the term "about" is intended to encompass + or −5%.

What is claimed is:

1. A method for making amphetamine-related products of formula (I):

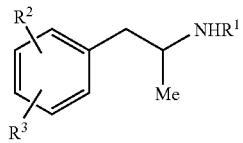

where $R^1$ is hydrogen or a lower alkyl group, and $R^2$ and $R^3$ are independently selected from hydrogen, halogen, lower alkyl groups, lower alkoxy groups, lower alkyl groups substituted with 1 to 5 halogens, lower alkoxy groups substituted with 1 to 5 halogens, or both $R^2$ and $R^3$, when on adjacent carbons, together constitute —O(CH$_2$)$_x$O— where x is an integer of 1 to 4, thereby forming a ring structure fused with the phenyl group, the method comprising:

dissolving a crude chlorinated phenylpropanolamine hydrochloride product of formula (II):

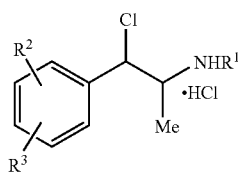

where $R^1$, $R^2$ and $R^3$ have the same meanings as identified above in connection with formula (I), in water to form an aqueous solution, contacting the aqueous solution with carbon, and hydrogenating the carbon-treated aqueous solution.

2. The method of claim 1 wherein the crude chlorinated phenylpropanolamine hydrochloride product of formula (II) is prepared from a phenylpropanolamine.

3. The method of claim 1 wherein the crude chlorinated phenylpropanolamine hydrochloride product of formula (II) is prepared by adding thionyl chloride to a solution of a phenylpropanolamine in an organic solvent.

4. The method of claim 3 wherein the organic solvent is toluene.

5. The method of claim 2 wherein the crude chlorinated phenylpropanolamine hydrochloride product of formula (II) is prepared by adding thionyl chloride to a solution of a phenylpropanolamine in an organic solvent.

6. The method of claim 5 wherein the phenylpropanolamine is norephedrine.

7. The method of claim 6 wherein the organic solvent is toluene.

8. The method of claim 3 wherein the phenylpropanolamine is norephedrine.

9. The method of claim 2 wherein the phenylpropanolamine is norephedrine.

10. The method of claim 6 wherein the norephedrine is selected from the group consisting of l-norephedrine, d-norephedrine and d,l-norephedrine.

11. The method of claim 8 wherein the norephedrine is selected from the group consisting of l-norephedrine, d-norephedrine and d,l-norephedrine.

12. The method of claim 9 wherein the norephedrine is selected from the group consisting of l-norephedrine, d-norephedrine and d,l-norephedrine.

13. The method of claim 6 wherein the norephedrine is l-norephedrine.

14. The method of claim 8 wherein the norephedrine is l-norephedrine.

15. The method of claim 9 wherein the norephedrine is l-norephedrine.

* * * * *